United States Patent [19]

Sezginer et al.

[11] Patent Number: 5,389,877
[45] Date of Patent: Feb. 14, 1995

[54] NUCLEAR MAGNETIC RESONANCE PULSE SEQUENCES FOR DETERMINING BOUND FLUID VOLUME

[75] Inventors: Abdurrahman Sezginer, Brookfield; Christian Straley, Ridgefield, both of Conn.

[73] Assignee: Schlumberger Technology Corporation, New York, N.Y.

[21] Appl. No.: 800,339

[22] Filed: Nov. 27, 1991

[51] Int. Cl.⁶ .............................................. G01V 3/00
[52] U.S. Cl. ..................................... 324/303; 324/307
[58] Field of Search ............... 324/303, 306, 307, 309, 324/314

[56] References Cited

U.S. PATENT DOCUMENTS

| | | | |
|---|---|---|---|
| 3,453,433 | 7/1969 | Alger et al. | 250/83.3 |
| 3,567,935 | 3/1971 | Nagel | 250/83.1 |
| 3,567,936 | 3/1971 | Tittman | 250/83.1 |
| 3,590,228 | 6/1971 | Burke | 235/151.35 |
| 3,638,484 | 2/1972 | Tixier | 73/152 |
| 3,896,668 | 7/1975 | Anderson et al. | 73/152 |
| 4,310,887 | 1/1982 | Suau | 364/422 |
| 4,686,364 | 8/1987 | Herron | 250/256 |
| 4,728,892 | 3/1988 | Vinegar et al. | 324/303 |
| 4,885,540 | 12/1989 | Snoddy et al. | 324/318 |
| 4,933,638 | 6/1990 | Kenyon et al. | 324/303 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |

OTHER PUBLICATIONS

L. Petrakis and E. Edelheit, "The utilization of nuclear magnetic resonance spectroscopy for petroleum, coal, oil shale, petrochemicals, and polymers. Phenomenology, paradigms of applications and instrumentation," *Applied Spectroscopy Reviews*, vol. 15 (1979), No. 2, pp. 196–260.

D. P. Gallegos et al., "A NMR Technique for the Analysis of Pore Structure: Application to Materials with Well-Defined Pore Structure," *Journal of Colloid and Interface Science*, vol. 119, No. 1, Sep. 1987, pp. 127–140 describes the use of NMR spin–lattice.

K. R. Brownstein and C. E. Tarr, "Importance of classical diffusion in NMR studies of water in biological cells," *Phys. Rev. A*, vol. 19, No. 6, pp. 2446–2453, 1979.

D. P. Gallegos and D. M. Smith, "A NMR Technique for the Analysis of Pore Structure: Determination of Continuous Pore Size Distributions," *J. Coll. Inther. Sci.*, 122, pp. 143–153, 1988.

W. E. Kenyon, J. J. Howard, A. Sezginer, C. Straley, A. Matteson, K. Horkowitz, R. Ehrlich, "Pore-Size Distribution of NMR in Microporous Cherty Sandstones," *Trans. SPWLA*, Paper LL, 1989.

J. J. Howard, W. E. Kenyon, and C. Straley, "Proton Magnetic Resonance and Pore Size Variations in Reservoir Sandstones," 65th Annual SPE Meeting, paper 20600, New Orleans, La., Sep. 1990.

C. Straley, C. E. Morriss, W. E. Kenyon, and J. J. Howard, "NMR in Partially Saturated Rocks: Laboratory Insights on Free Fluid Index and Comparison with Borehole Logs," SPWLA 32nd Annual Logging Symposium, Jun. 16–19, 1991.

(List continued on next page.)

*Primary Examiner*—Louis Arana
*Attorney, Agent, or Firm*—Leonard W. Pojunas

[57] ABSTRACT

An NMR pulse sequence for use in a borehole logging tool includes a series of CPMG pulses according to:

$$T_r - 90°\pm x - (t_{cp} - 180°y - t_{cp} - \text{echo}_j)$$

where j is the index of CPMG echoes gathered, $T_r$ is wait time, $t_{cp}$ is the Carr-Purcell spacing. This pulse sequence is used to determine Bound Fluid Volume (BFV) which is subtracted from total porosity to yield Unbound Fluid Volume (UFV) of a formation surrounding the borehole. Measuring the BVF, the amount of rapidly relaxing fluid (less than 50 ms), is more efficient than measuring UFV (up to 2 secs), and is insensitive to motion of the logging tool.

18 Claims, 4 Drawing Sheets

OTHER PUBLICATIONS

T. C. Farrar and E. D. Becker, *Pulse and Fourier Transform NMR*, p. 27, Academic Press, 1971.

R. J. S. Brown and B. W. Gamson, "Nuclear Magnetism Logging," AIME (1960) 219, pp. 201–219.

C. H. Neuman and R. J. S. Brown, "Applications of Nuclear Magnetism Logging to Formation Evaluation," *J. of Pet. Tech.*, vol. 34, pp. 2853–2862, 1982.

R. N. Chandler, W. E. Kenyon and C. E. Morriss, "Reliable Nuclear Magnetism Logging: Effective Porosity and Residual Oil Saturation", SPWLA 28th Annual Logging Symposium, Jun. 29–Jul. 2, 1987 Transactions, vol. I, Manuscript C.

M. N. Miller et al., "Spin Echo Magnetic Resonance Logging: Porosity and Free Fluid Index Determination," SPE 20561, vol. $\Omega$, Proceedings of the 1990 Society of Petroleum Engineers Annual Technical Conference, Sep. 23–26, New Orleans, La., 1990.

G. R. Coates et al., "An Investigation of a New Magnetic Resonance Imaging Log," paper DD, vol. II, SPWLA 32nd Annual Logging Symposium Midland, Tex., Jun. 16–19, 1991.

G. R. Coates et al., "The Magnetic Resonance Imaging Log Characterized by Comparison With Petrophysical Properties and Laboratory Core Data," SPE 22723, vol. $\Omega$, Proceedings of the 1991 Society of Petroleum Engineers Annual Technical Conference, Oct. 6–9, Dallas, Tex., 1991.

NUCLEAR MAGNETIC RESONANCE PULSE SEQUENCES FOR DETERMINING BOUND FLUID VOLUME

FIELD OF THE INVENTION

The invention concerns nuclear magnetic resonance (NMR) pulse sequences which are used in evaluating earth formations. More specifically, the invention relates to NMR pulse sequences which are used by a well logging tool for measuring earth formation properties.

BACKGROUND OF THE INVENTION

Nuclear magnetic logging tools, such as disclosed in U.S. Pat. Nos. 4,933,638 to Kenyon et al. for "Borehole Measurement of NMR Characteristics of Earth Formations, and Interpretations Thereof"; and 5,055,787 and 5,055,788 both to Kleinberg et al. for "Borehole Measurement of NMR Characteristics of Earth Formations", measure the number and nuclear magnetic resonance (NMR) relaxation rates of hydrogen atoms in the pore space of rocks by measuring the amplitude and decay rate of signals resulting from pulse-echo sequences. In essence, the nuclear magnetic logging tools send a stream of RF-pulses into the formation and monitor the returning pulses which are called spin echoes. The measurements made are typically cyclical, with each cycle taking several seconds. Interpretation algorithms are then used to find the formation properties of interest.

The signal measured by a nuclear magnetic logging tool, such as the Pulsed Nuclear Magnetism Tool (PNMT, mark of Schlumberger) is proportional to the mean density of hydrogen nuclei in the fluid that occupies the pore-space. Hydrogen nuclei in the rock matrix relax too rapidly and are not detected by the tool. Since the hydrogen density in water and liquid hydrocarbons are approximately constant, the detected signal can be calibrated to give the volume fraction of the fluid occupying the pore space.

NMR relaxation of a water saturated porous rock is not a simple exponential relaxation, but it is a continuous superposition of exponential relaxations. For example, in an inversion-recovery experiment, the signal obtained after an inversion and a recovery time of length t is $$m(t) = \int_0^\infty a(T_1)(1 - 2e^{-t/T_1})dT_1 \quad (1)$$

Loosely speaking, $a(T_1)dT_1$ is the volume fraction of the fluid whose relaxation time is between $T_1$ and $T_1 + dT_1$, where $T_1$ is spin-lattice relaxation time. This interpretation is only approximately correct because any isolated pan of the pore-space has a multi-exponential relaxation [1]. However, pores of rocks are in a fast diffusion regime where the signal is approximately single-exponential, and the relaxation time is proportional to the volume to surface ratio. Several researchers have demonstrated for water saturated sandstones that the pore size distribution is closely related to the distribution of NMR relaxation times [2–4].

Short relaxations times are due to water that is bound to clay minerals or water in pores that are too small to be flushed by a feasible pressure gradient. Also, heavy (viscous) hydrocarbons have shorter relaxation times. Fluids that relax slowly have low viscosity and reside in large pores. Hence, the slowly relaxing fluids can be produced provided there is sufficient permeability. It is therefore important to quantify the volume of the slowly relaxing fluids.

OBJECTS AND SUMMARY OF THE INVENTION

It is an object of the invention to provide an NMR pulse sequence which indicates bound and thus unbound fluid volume of a logging borehole environment.

In a specific embodiment of a novel technique, the inventors have found that estimating the bound fluid volume by measuring the amount of rapidly relaxing fluid is more efficient compared to directly measuring the unbound fluid volume. This novel technique is insensitive to motion of the PNMT tool in the borehole. If the total porosity is known, producible volume can be obtained by subtracting the bound fluid volume from the total porosity.

This invention concerns a method for measuring an indication of an attribute of a volume of earth formation with a borehole tool. The tool includes a means for producing static magnetic fields in a volume of a formation, means for producing oscillating magnetic fields in a volume of a formation, and means for measuring an induced magnetic signal. Steps of the method include:
a) producing a static magnetic field in the volume of formation;
b) producing oscillating magnetic fields according to a pulse sequence $$T_r - 90°_{\pm x} - (t_{cp} - 180°_y - t_{cp} - \text{echo}_j)$$

where $j = 1, 2, \ldots J$, and J is the number of echoes collected in a single Carr-Purcell-Meiboom-Gill (CPMG) sequence in order to induce signals in the volume which are measurable by the tool in the borehole;
where $T_r$ is recovery time before a CPMG sequence, and
where $t_{cp}$ is the Carr-Purcell spacing;
c) measuring with the tool the induced signals; and
d) determining from the measured signals an indication of bound fluid volume of the volume of earth formation.

DETAILED DESCRIPTION OF THE INVENTION

Measuring formation properties, such as spin-lattice relaxation time (T1); spin—spin relaxation time (T2) and total porosity ($\Phi$) using NMR logging tools are described in U.S. Pat. No. 5,023,551 to Kleinberg et al. for "Nuclear Magnetic Resonance Pulse Sequences for Use with Borehole Logging Tools". The specification of U.S. Pat. No. 5,023,551 is incorporated by reference and is assigned to the same assignee as this invention.

Producible fluids in porous rocks are distinguished by their slow Nuclear Magnetic Resonance (NMR) relaxation times. However, to measure the producible fluid (the unbound fluid volume (UFV)) requires an immense amount of data gathering of relaxation times, many of which can reach the order of 2 seconds, using numerous iterations of the pulse sequence described in U.S. Pat. No. 5,023,551 and a subsequent interpretation of that great amount of data. Such a technique is relatively time consuming and prohibits logging at speeds that are standard in the business (1800–3600 ft/hr). Rapidly relaxing fluids (less than 50 ms, for example) are bound to the rock, so they are not producible. The inventors have found that NMR can be used to estimate the unbound fluid volume (UFV). Specifically, using NMR well logging techniques, bound fluid volume (BFV) is measured, and subtracted from total porosity $\Phi$ to estimate unbound fluid volume (UBV). The estimation of UBV indicates the amount of producible fluid in a formation being logged.

Bound and unbound fluid volumes are defined as:

$$BFV = \int_0^{T_c} a(T_1)dT_1 \quad (2)$$

$$UFV = \int_{T_c}^{\infty} a(T_1)dT_1 \quad (3)$$

$$BFV = UFV = \Phi \quad (4)$$

where $\Phi$ is porosity, the total volume fraction of fluids in the rock. The cutoff relaxation time $T_c$ distinguishing BFV from UFV is empirically determined to be 50 ms for water saturated sandstones. The UFV computed from (3) has been shown to correlate well with the volume of water that can be centrifuged out of the sample at a fixed pressure gradient [5]. The approach used in [5] to evaluate UFV involves finding the function $a(T_1)$, which is a time consuming process hence unsuitable for logging at moderate speeds.

Since BFV is associated with rapidly relaxing components, less than the cutoff time of 50 ms, for example, BFV can be measured faster than UFV. Determining UFV requires measurement of slowly relaxing components from 50 ms up to 2 seconds. If the total porosity $\Phi$ is known from some other measurement, UFV can be obtained by subtracting BFV from the total porosity.

Figure 1:
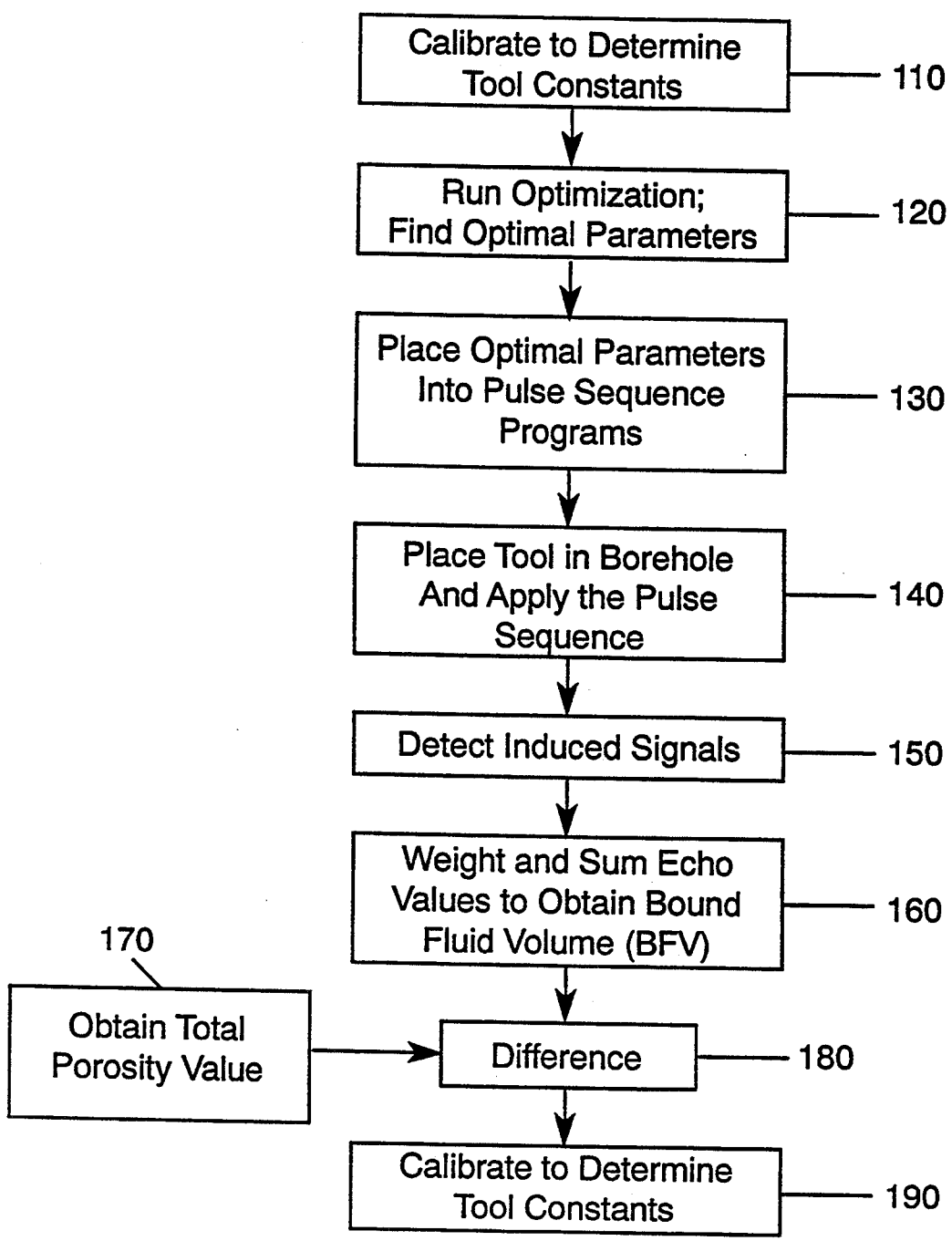
FIG. 1 is a flow chart illustrating steps for determining Bound Fluid Volume (BFV) and Unbound Fluid Volume (UFV) of a formation.

FIG. 1 is a flow chart illustrating steps for determining Bound Fluid Volume (BFV) of a formation. At 110, a calibration is performed to determine tool constants. At 120, desired parameters are entered, and an optimization is performed to find the optimal parameters. Specifically, the accuracy of the BFV estimate is optimized: the most accurate measurement is determined for a given amount of time. See the discussion below concerning Equation (11). At 130, the optimal parameters are used in pulse sequence programs. Steps 110 and 130 are described in U.S. Pat. No. 5,023,551 to Kleinberg et al. At 140, a PNMT logging tool, for example, is placed in the borehole. The PNMT produces a static magnetic field in the volume of formation and then produces oscillating magnetic fields according to a pulse sequence $$T_r - 90°_{\pm x} - (t_{cp} - 180°_y - t_{cp} - \text{echo}_j)$$

where $j=1, 2, \ldots J$, and J is the number of echoes collected in a single Carr-Purcell-Meiboom-Gill (CPMG) sequence to induce signals in the volume which are measurable by the PNMT in the borehole; where $T_r$ is recovery time before a CPMG sequence, and where $t_{cp}$ is the Carr-Purcell spacing. The pulse sequence is obtained by the optimization procedure of step 120. This pulse sequence is also discussed below concerning equations (5) and (6). At 150, the PNMT tool then detects resulting signals which have been induced in the formation around the borehole. At 160, echo values are weighted and summed as discussed below concerning equation (2) and FIG. 2, for example. At 170, total porosity is obtained. Total porosity can be obtained with the PNMT itself. However, logging for porosity with this tool is relatively time consuming. In a preferred technique, total porosity is obtained using a Litho Density Tool (LDT, mark of Schlumberger), Compensated Neutron Log (CNL, mark of Schlumberger) or Sonic tool. Examples of tools for obtaining porosity are described in U.S. Pat. Nos. 3,453,433 to Alger et al. and 4,686,364 to Herron; 3,567,936 to Tittman and 3,567,935 to Nagel; and 3,590,228 to Burke and 3,896,668 to Anderson et al. U.S. Pat. Nos. 3,638,484 to Tixier and 4,310,887 to Suau describe deriving porosity data using density, neutron and sonic tools. At 180, the difference between the total porosity $\Phi$ obtained in step 170 and the bound fluid volume (BFV) obtained at step 160 yields unbound fluid volume UFV at 190. UFV indicates the amount of producible fluid that is contained in the formation around the borehole being logged.

According to this invention, phase-alternated Carr-Purrcell-Meiboom-Gill (CPMG) sequences [6] are used, which are separated by a fixed, relatively short recovery time ($T_r = 20$ ms):

$$T_r \text{CPMG}^{(+)} T_r \text{CPMG}^{(-)} T_r \text{CPMG}^{(+)} T_r \text{CPMG}^{(-)} \quad (5)$$

where each CPMG sequence yields a short train of spin-echoes:

$$\text{CPMG}^{(\pm)} = 90°_{\pm x} [t_{cp} \, 180°_y t_{cp} \pm \text{echo}_j] \text{ repeat for } j=1, 2, \ldots, J \quad (6)$$

and $t_{cp}$ is half of the echo spacing (about 0.2 ms). $90°_{\pm x}$ denotes an RF-pulse that causes the spins to rotate by a 90° angle about the axis $\pm x$. Similarly $180°_y$ denotes an RF-pulse that causes a rotation by 180° about the axis y. The z-axis is parallel to the static field, the x-axis is in the direction of the circularly polarized component of the RF-field ($B_1$) that rotates in the same direction as the spins precess. The reference frame (x,y,z) rotates around the z axis with the angular frequency of the RF-field.

An estimate of the BFV is obtained by a weighted sum of the echoes:

$$\overline{BFV} = \sum_{j=1}^{J} w_j \text{echo}_j \quad (7)$$

The overbar denotes the estimate of the BFV as opposed to the quantity defined in (2).

Figure 2:
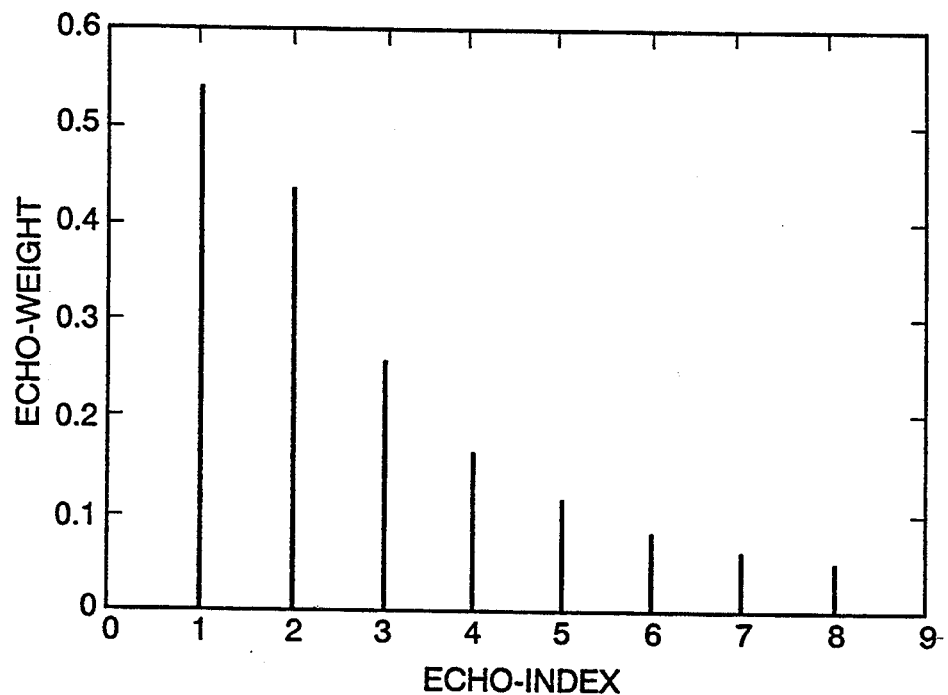
FIG. 2 is a chart illustrating an example of values of the weights applied to pulse echoes to obtain BFV.

FIG. 2 is a chart illustrating an example of values of weights applied to echoes to obtain BFV. Echo-Weight is plotted as a function of Echo-Index. These Echo- Weights were applied to echoes to obtain $\overline{BFV}$ for Carr-Purcell spacing $t_{cp}=0.2$ ms and the ratio of spin-lattice relaxation time to spin—spin relaxation time $T_1/T_2$ is 1.5. The variance of the estimate after stacking for T seconds is $$\text{Var}[\overline{BFV}] = \frac{T_r + 2Jt_{cp}}{T} \sigma^2 w^2 \qquad (8)$$

$$w^2 = w_1^2 + w_2^2 + \ldots + w_J^2$$

where each echo has independently and identically distributed, zero-mean, additive Gaussian noise of standard deviation $\sigma$, which is about 10 porosity units for the PNMT. $T_r$ is the length of the recovery-time in between the CPMG sequences. w is the norm of the vector $w=(w_1, w_2, \ldots, w_J)$. The estimator of BFV is a linear functional that acts on the relaxation-time distribution:

$$\overline{BFV} = \int_0^\infty f(T_1)a(T_1)dT_1 \qquad (9)$$

where $f(T_1)$ is a weighting function (not to be confused with the echo-weights $w_j$):

$$f(T_1) = [1 - e^{-T_r/T_1}] \sum_{j=1}^{J} w_j \exp\left(\frac{-2jt_{cp}(T_1/T_2)}{T_1}\right) \qquad (10)$$

The above expression is simplified by the fact that the ratio $T_1/T_2$ is approximately constant. It is unity for bulk water samples and about 1.5 for water saturated sandstones.

Also taken into account in the computation, but not shown in (10), is the fact that in a CPMG pulse-echo sequence the first spin-echo is about 61% of what would be expected from the extrapolation of the other echoes. This is a consequence of spin-dynamics in inhomogeneous fields and it has been verified by numerical solutions of Bloch's equation. The factor 61% was experimentally determined.

The adjustable parameters of the measurement, namely, $(w_1, w_2, \ldots, w_J)$, $T_r$, J are determined by two competing requirements. First, according to (2) and (9), $$f(T_1) \approx \begin{cases} 1, & \text{if } T_1 < T_c \\ 0, & \text{if } T_1 > T_c \end{cases} \qquad (11)$$

must be satisfied. On the other hand, according to (8), w must be kept small in order to keep the statistical error small. Equation (11) has been solved for w in the least square sense subject to the constraint w<constant. The parameters $T_r$ and J have been determined by trial and error to minimize the least square error in (11). The result of the optimization yielded $J=8$, $T_r=20$ ms and a set of weights $w_j$ that decrease with increasing j which are shown in FIG. 1.

Figure 3:
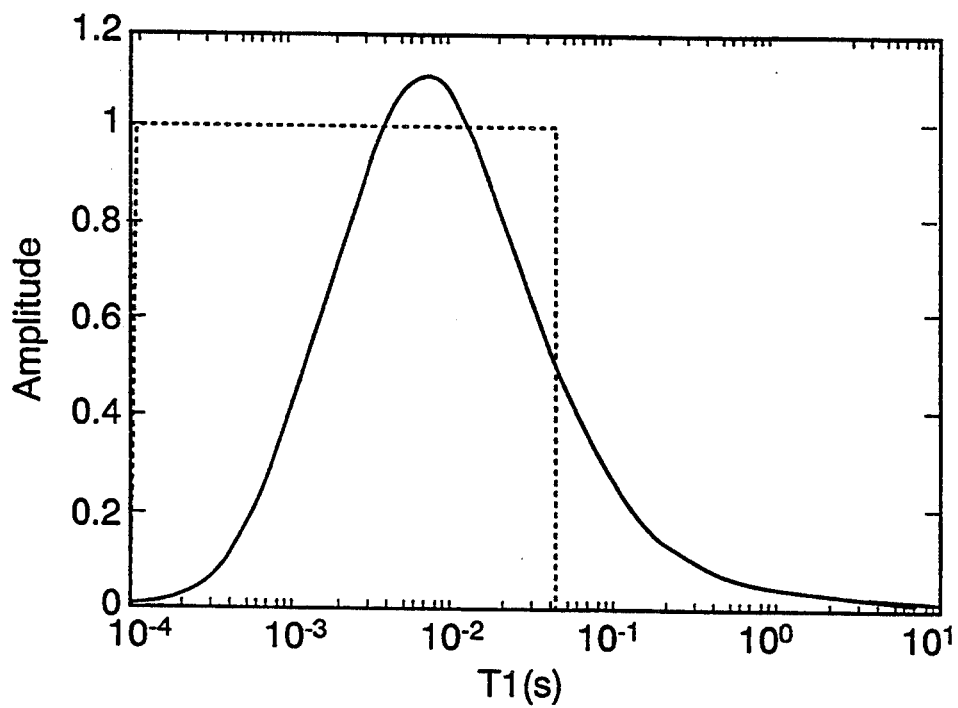
FIG. 3 is a chart illustrating an example of actual and ideal weighting functions.

FIG. 3 is a chart illustrating an example of actual and ideal weighting functions. Amplitude is plotted as a function of spin lattice relaxation time $T_1$ in seconds. The solid line shows an actual weighting function $f(T_1)$ and the dashed line shows an ideal weighting function. In this case, $t_{cp}=0.2$ ms, recovery time $T_r=20$ ms, $J=8$, $T_1/T_2=1.5$, and the weights are as shown in FIG. 2. As intended, the weighting function has a long-time cut-off because slowly relaxing components can not recover in the short recovery time. There is also a short-time cut-off (see FIG. 3) because the components that significantly decay before the first echo are not observed.

A short-time cut-off is needed so that the tool is insensitive to hydrogen in the rock matrix. The short-time cut-off around 1 ms shown in FIG. 3 is probably higher than needed: some clay-bound water may be missed. However, if the total porosity measurement has the same short-time cut-off, no error will be introduced in the estimation of UFV. Noise performance of the estimator of the bound fluid volume follows:

For $t_{cp}=0.2$ ms, $T_r=20$ ms, $J=8$, $\sigma=10$ p.u., and signal accumulation time $T=1$ s, the standard deviation of BFV is 1.2 p.u. For $t_{cp}=0.35$ ms, the standard deviation is 1.4 p.u.

EXPERIMENTAL VERIFICATION: NICL SOLUTIONS

To verify the present theory, the inventors have applied the proposed measurement to NiCl solutions of known relaxation times. The k th sample has the relaxation time $T_{1k}$ and its relaxation time distribution $a_k(T_1)$.

$$a_k(T_1) = \delta(T_1 - T_{1k}) \qquad (12)$$

where $\delta$ denotes the Dirac-delta distribution. According to (9), the BFV estimate for such a sample should be:

$$(\overline{BFV})_k = f(T_{1k}) \qquad (13)$$

Figure 4:
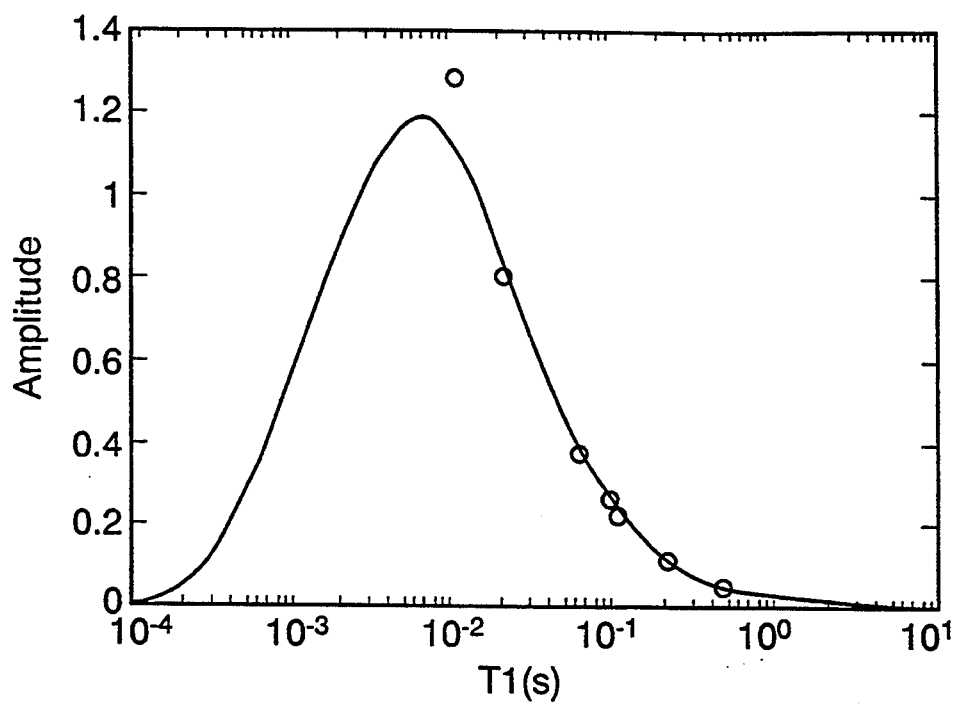
FIG. 4 is a chart illustrating the weighting function and measurements on NiCl solutions.

The function f above is different from the one shown in FIG. 3 because $T_1=T_2$ for bulk NiCl solutions. In FIG. 4, the experimental results are compared to Equation (10).

FIG. 4 is a chart illustrating the weighting function and measurements on NiCl solutions. Amplitude is plotted as a function of $T_1$ in seconds. The solid line shows a weighting function for $T_1=T_2$. Actual measurements of NiCl solutions are plotted on the chart as circles. A close correlation between the NiCl measurements and the weighting function is evident.

EXPERIMENTAL VERIFICATION: SANDSTONES

The proposed sequence was applied to 42 water saturated sandstones. $\overline{BFV}$ was determined as described above and it was subtracted from the total porosity to obtain an estimate of UFV. The total porosity was determined by weighing the sample water saturated, in air; water saturated, immersed in water; and dry, in air.

To obtain an experimental estimate of the producible volume the samples were centrifuged. The samples were centrifuged for 60 minutes, reversed, and centrifuged for 30 minutes. The rate of rotation was 4000 rpm which produced about 100 psi pressure difference across the 3.75 mm length of the samples. The amount of water that was expelled from each sample was determined by weighing the sample. The difference $\Phi - \overline{BFV}$ is an estimate of UFV, and it correlates well with the volume of fluid that was centrifuged out of the samples as shown in FIG. 4.

Figure 5:
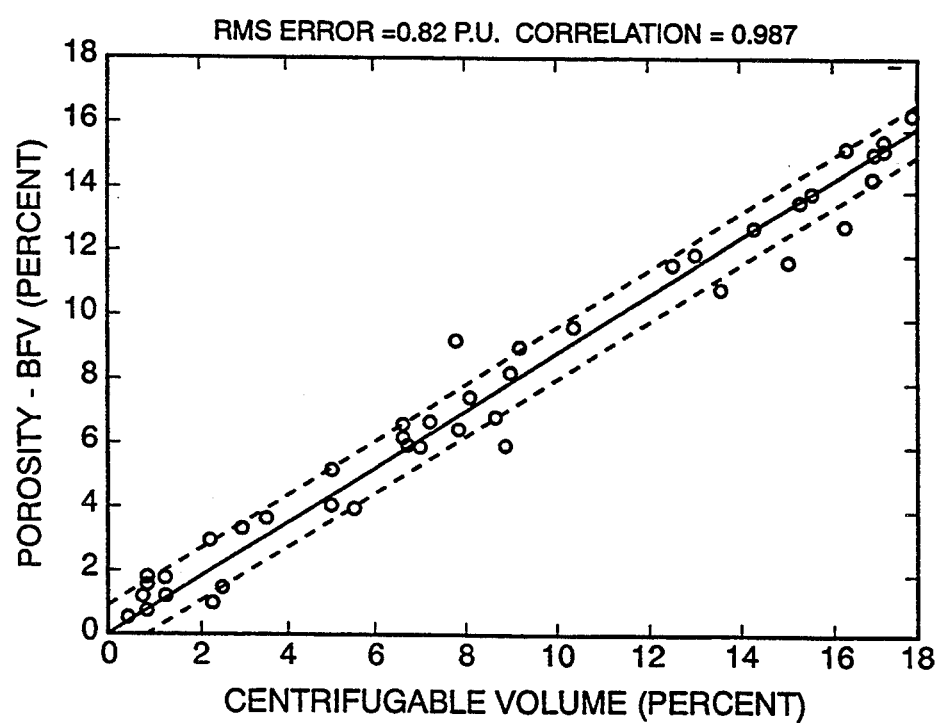
FIG. 5 is a chart illustrating the correlation of total porosity minus BFV to centrifugable water.

FIG. 5 is a chart illustrating the correlation of total porosity minus BFV to centrifugable water. Total porosity (percent) is plotted as a function of centrifugable volume (percent). Each rock specimen is shown by a circle on the graph. The solid line is the best linear fit that goes through the origin. The dashed lines are drawn parallel to the solid line, one standard deviation above and below it. RMS error is 0.82 P.U. and correlation is 0.987.

MOTION EFFECT

For a crude computation of the motion effect, the inventors postulate that the RF magnetic field is uniform in a sensitive region $0<z<L$ and zero elsewhere. The static magnetic field is uniform in the region $-p<z<L$. In this notation, z is the depth coordinate with respect to a fixed point on the tool. L is the length of the sensitive region and p is the length of the prepolarization region immediately above the sensitive region.

At the beginning of a CPMG, the longitudinal magnetization is $$M_z(z)/M_0 = \begin{cases} 1 - \exp\left(-\frac{(z+p)}{(vT_1)}\right), & \text{for } -p < z < vT_r \\ 1 - \exp\left(-\frac{T_r}{T_1}\right), & \text{for } vT_r < z < L \end{cases} \quad (14)$$

where $M_0$ is the equilibrium magnetization and v is the logging speed. The first region $(-p<z<vT_r)$ has not been subject to RF pulses yet. The second region $(vT_r<z<L)$ has been subject to a CPMG sequence. The approximation is made that the magnetization is zero at the end of a CPMG sequence (Actually, there is some remaining transverse magnetization that is quickly dephased). The transverse magnetization at the peak of the j th echo is:

$$M_\perp(z)/M_0 = \exp^{(-\frac{2jt_{cp}}{T_2})}\left[1 - \exp\left(-\frac{z+p-2vjt_{cp}}{vT_1}\right)\right], \quad (15)$$

for $\min(L, 2vjt_{cp}) < z < \min(L, vT_r + 2vjt_{cp})$, $$\exp^{(-\frac{2jt_{cp}}{T_2})}\left[1 - \exp\left(-\frac{T_r}{T_1}\right)\right],$$

for $\min(L, vT_r + 2vjt_{cp}) < z < L$.

Therefore, the weighting function $f(T_1)$ is modified as follows in the presence of motion:

$$f(T_1, v) = \quad (16)$$

$$\sum_{j=1}^{J} w_j e^{-2jt_{cp}/T_2} \frac{1}{L}\left[(1 - e^{-T_r/T_1})\max(0, L - vT_r - 2vjt_{cp}) + \right.$$

$$\min(L, vT_r + 2vjt_{cp}) - \min(L, 2vjt_{cp}) +$$

$$\exp\left(-\frac{\min(p+L-2vjt_{cp}, p+vT_r)}{vT_1}\right)vT_1 -$$

$$\left.\exp\left(-\frac{\min(p+L-2vjt_{cp}, p)}{vT_1}\right)vT_1\right]$$

Figure 6:
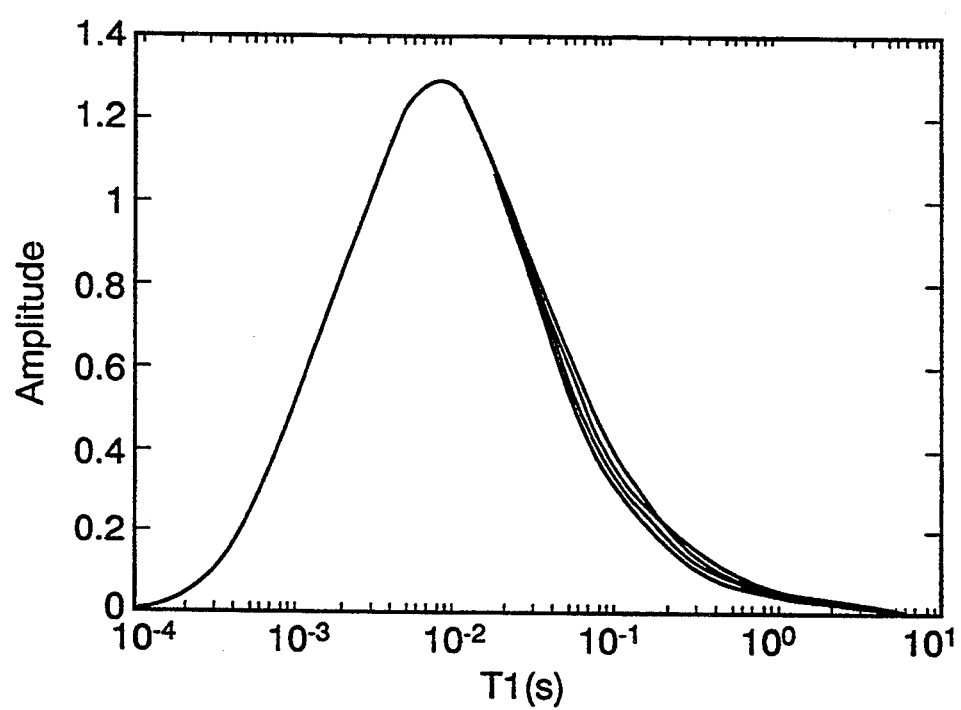
FIG. 6 is a chart illustrating that logging speed has little effect on the weighting function.

FIG. 6 is a chart illustrating that logging speed has little effect on the weighting function. Weighting function is plotted as a function of $T_1$ in seconds. The logging speed is $\{0, 1, 2, 4\}$ apertures/second, increasing from the bottom to the top of the curve. For a six inch aperture, these speeds correspond to 0, 1800, 3600, 7200 ft/hr. $p=L/2$ and $T_1/T_2=1.5$ where p is the length of the prepolarization region.

As shown in FIG. 6, sonde motion slightly increases the emphasis at the longer relaxation times (20 ms$<T_1<$1 s). This is because at moderate speeds, the magnetization that moves from the prepolarization region into the sensitive region is larger than the magnetization that leaves the sensitive region (the first term on the right hand side of Equation 14 is larger than the second). The motion effect is small even at high logging speeds such as 7200 ft/hr, because the measurement sequence is only 23 ms long.

REFERENCES

1. K. R. Brownstein and C. E. Tarr, "Importance of classical diffusion in NMR studies of water in biological cells," *Phys. Rev. A*, Vol. 19, No. 6, p. 2446-2453, 1979.

2. D. P. Gallegos and D. M. Smith, "A NMR Technique for the Analysis of Pore Structure: Determination of Continuous Pore Size Distributions," *J. Coll. Inther. Sci.*, 122, p 143-153, 1988.

3. W. E. Kenyon, J. J. Howard, A. Sezginer, C. Straley, A. Matteson, K. Horkowitz, R. Ehrlich, "Pore-Size Distribution and NMR in Microporous Cherty Sandstones," *Trans. SPWLA*, Paper LL, 1989.

4. J. J. Howard, W. E. Kenyon, and C. Straley, "Proton Magnetic Resonance and Pore Size Variations in Reservoir Sandstones," 65th Annual SPE Meeting, paper 20600, New Orleans, La., September 1990.

5. C. Straley, C. E. Morriss, W. E. Kenyon, and J. J. Howard, "NMR in Partially Saturated Rocks: Laboratory Insights on Free Fluid Index and Comparison with Borehole Logs," presented at the annual SPWLA meeting, Midland, Tex., 1991.

6. T. C. Farrar and E. D. Becker, *Pulse and Fourier Transform NMR*, p. 27, Academic Press, 1971.

We claim:

1. A method involving nuclear magnetic resonance (NMR) for measuring an indication of an attribute of a volume of earth formation with a borehole tool for placement in a borehole in the earth formation such that the borehole tool is substantially surrounded by the earth formation, wherein the borehole tool produces static magnetic fields in a volume of a formation, produces oscillating magnetic fields in a volume of a formation, and measures an induced magnetic signal, the method comprising:
   a) producing a static magnetic field from the borehole tool into the volume of formation substantially surrounding the borehole tool oscillating magnetic fields according to a pulse sequence
   b) the borehole tool also producing oscillating magnetic fields according to a selected pulse sequence in order to induce signals in the volume which are measurable by the tool in the borehole;
   c) defining an NMR cutoff relaxation time;
   d) measuring with the tool the induced signals; and
   e) determining from the measured signals occurring substantially before the cutoff relaxation time an indication of bound fluid volume (BFV) of the volume of earth formation.

2. A method according to claim 1, wherein: the induced signals comprise at least spin-echoes, and the step of measuring the induced signals comprises integrating at least portions of the echoes.

3. The method of claim 2, including weighting and summing echo values to obtain BFV.

4. The method of claim 3, including:
obtaining a total porosity value of the earth formation; and
subtracting the BFV from the total porosity value to obtain Unbound Fluid Volume.

5. The method of claim 4, including measuring with the tool induced signals which correspond to relaxation times below a cutoff relaxation time to determine the indication of BFV.

6. The method of claim 5, wherein the induced signals correspond to relaxation times of fluids bound within the formation.

7. The method of claim 6, wherein the cutoff relaxation time is approximately 50 milliseconds.

8. The method of claim 7, wherein the borehole tool is moved upward through the borehole at a speed of 1800 ft/hr and greater, and the weighting of the echo values is substantially independent of the speed of the borehole tool.

9. A method for measuring an indication of an attribute of a volume of earth formation with a borehole tool for placement in a borehole in the earth formation such that the borehole tool is substantially surrounded by the earth formation, wherein the borehole tool produces static magnetic fields in a volume of a formation, produces oscillating magnetic fields in a volume of a formation, and measures an induced magnetic signal, the method comprising:

a) producing a static magnetic field from the borehole tool into the volume of formation substantially surroundng the borehole tool;

b) producing oscillating magnetic fields according to a pulse sequence $$T_r - 90°_{\pm x} - (t_{cp} - 180°_y - t_{cp} - \text{echo}_j)$$

where $j = 1, 2, \ldots J$, and J is the number of echoes collected in a single Carr-Purcell-Meiboom-Gill (CPMG) sequence in order to induce signals comprising at least CPMG spin-echoes in the volume which are measurable by the tool in the borehole;
where $T_r$ is recovery time before a CPMG sequence, and
where $90°_{\pm x}$ *indicates rotation by* $90°$ about an axis $\pm x$;
where $t_{cp}$ is the Carr-Purcell spacing;
where $180°_y$ indicates rotation by $180°$ about a y axis;

c) measuring with the tool the induced signals by integrating at least portions of the CPMG echoes wherein the induced signals correspond to nuclear magnetic resonance relaxation times below a cutoff relaxation time of 50 ms; and d) determining from the measured signals an indication of bound fluid volume (BFV) of the volume of earth formation by weighting and summing echo values.

10. The method of claim 9, wherein the weighting of the echo values decreases with increasing "j".

11. The method of claim 10, wherein the borehole tool is moved upward through the borehole at a speed of 1800 ft/hr and greater, and the weighting of the echo values is substantially independent of the speed of the borehole tool.

12. A method for measuring an indication of an attribute of a volume of earth formation with a borehole tool for placement in a borehole in the earth formation, the steps comprising:

a) producing a static magnetic field from the borehole tool into the formation;

b) producing oscillating magnetic fields from the borehole tool according to a selected pulse sequence in order to induce signals in the formation which are measurable by the borehole tool in the borehole;

c) measuring with the borehole tool the induced signals which correspond to relaxation times in substantially two time periods occurring before and after a cutoff relaxation time; and d) determining from the measured signals occurring in one time period of the two time periods an indication of unbound fluid volume (UFV) of the volume of earth formation.

13. The method of claim 12, wherein the induced signals in the one time period occur substantially after the cutoff relaxation time and correspond to relaxation times of fluids unbound in the formation which indicate UFV.

14. The method of claim 12, wherein the induced signals in the one time period occur substantially before the cutoff relaxation time and correspond to relaxation times of fluids bound within the formation, indicating bound fluid volume (BFV), the steps including:
obtaining a total porosity value of the earth formation; and
subtracting the BFV from the total porosity value to obtain UFV.

15. A method according to claim 14, wherein the induced signals comprise at least spin-echoes, and the step of measuring the induced signals comprises integrating at least portions of the echoes.

16. The method of claim 15, including weighting and summing echo values to obtain BFV.

17. The method of claim 16, wherein the cutoff relaxation time is approximately 50 milliseconds.

18. The method of claim 17, wherein the borehole tool is moved upward through the borehole at a speed and the weighting of the echo values is substantially independent of the speed of the borehole tool.

* * * * *